United States Patent [19]
Gordon

[11] 4,065,973
[45] Jan. 3, 1978

[54] LIQUID SAMPLER
[75] Inventor: Abraham Gordon, Teaneck, N.J.
[73] Assignee: Technicon Instruments Corporation, Tarrytown, N.Y.
[21] Appl. No.: 749,556
[22] Filed: Dec. 10, 1976
[51] Int. Cl.² ............................................. G01N 1/12
[52] U.S. Cl. ................................................. 73/423 A
[58] Field of Search ..................................... 73/423 A
[56] References Cited
FOREIGN PATENT DOCUMENTS
982,968  2/1965  United Kingdom .............. 73/423 A Primary Examiner—S. Clement Swisher
Attorney, Agent, or Firm—S. P. Tedesco

[57] ABSTRACT

A sampler is provided having a liquid sampling probe. A drive mechanism for the probe includes a screw element and a nut element threaded thereon, one of which elements is axially fixed and driven to axially raise and lower the other element which supports the probe. In one axial position of the element supporting the probe, the last-mentioned element is moved between first and second angular positions thereof.

4 Claims, 6 Drawing Figures

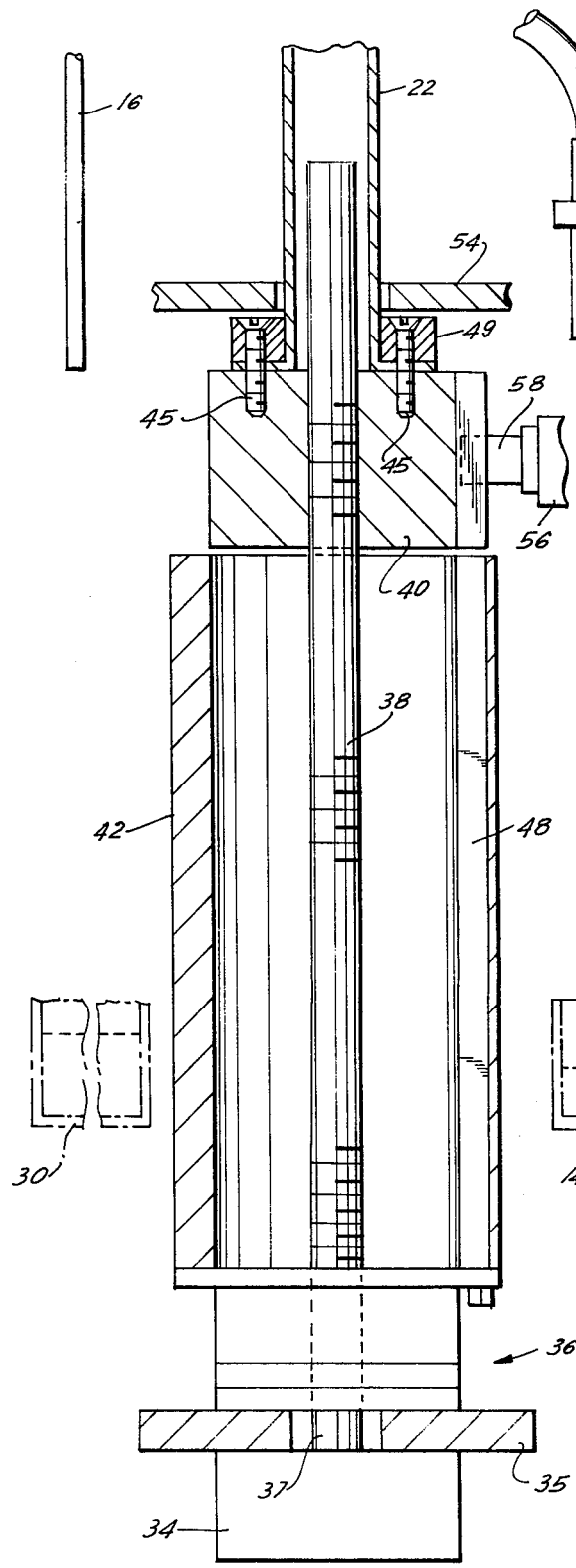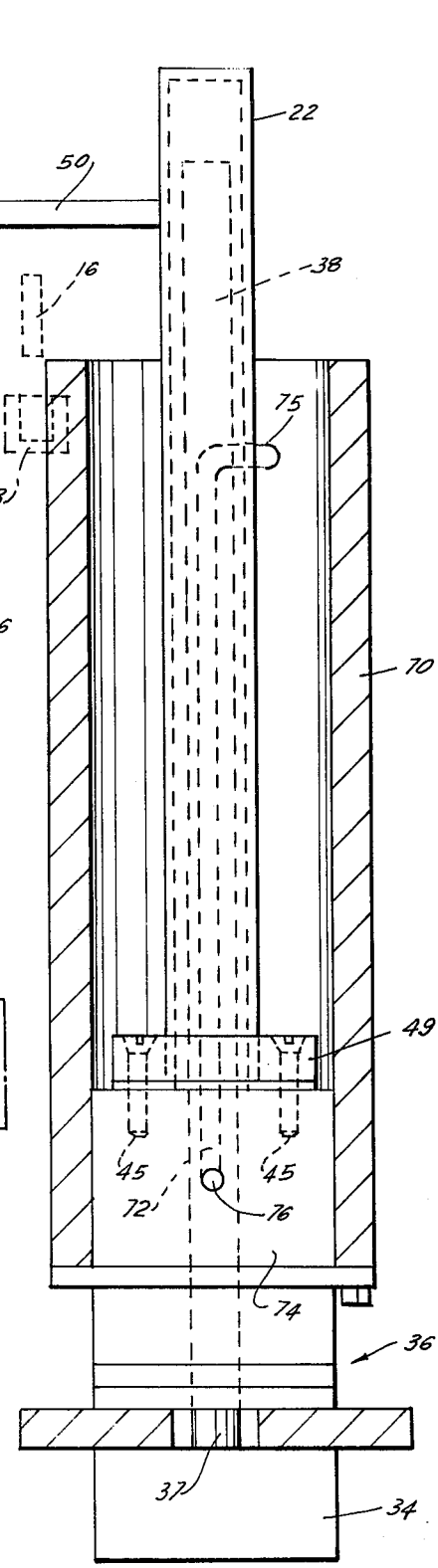

LIQUID SAMPLER

This invention relates to a drive mechanism for a probe in a sampler useful in automated sample analysis, which probe is lowered into and raised from successive liquid containers. The probe is also moved when in the raised condition from one angular position to at least one other angular position.

Heretofore, an aspirating probe has been associated with a sampler for the supply of a series of liquid samples for analysis seriatium. The samples may be a series of discrete blood specimens, supported in a series of cups mounted on a motor driven turntable of the sampler. The probe has been provided with a drive mechanism for movement of the probe into the cup then indexed to an offtake station for aspiration of the sample and then usually into a wash liquid solution within a stationery wash receptacle associated with the sampler for aspiration of wash solution before the probe enters the next sample cup. Isreeli et al. U.S. Pat. No. 3,251,229 and de Jong U.S. Pat. No. 3,134,263 describe what are believed to be typical probe drive mechanisms for accomplishment of these probe movements. The drive mechanisms are relatively complex and expensive. The present invention contemplates the provision of a simple and relatively inexpensive drive mechanism which may accomplish these same probe movements.

It is an object of the invention to provide an improved probe driving mechanism for use in automated sample analysis. A further object is to provide a simplified and relatively inexpensive drive mechanism for such a probe. In accordance with one aspect of the invention, the drive mechanism includes a screw element and a nut element threaded thereon, one of which elements is axially fixed and driven to raise and lower the other element which supports a probe. In one axial position, the probe-carrying element is moved bodily with the driving member from one angular position to another. Further objects of the invention will be apparent from the following detailed description of the presently preferred embodiments of the invention.

In the drawings:

FIG. 5 is a sectional view on line 5—5 of FIG. 2; and

FIG. 6 is a sectional view similar to FIG. 3 showing a modified form of the invention.

Figure 1:
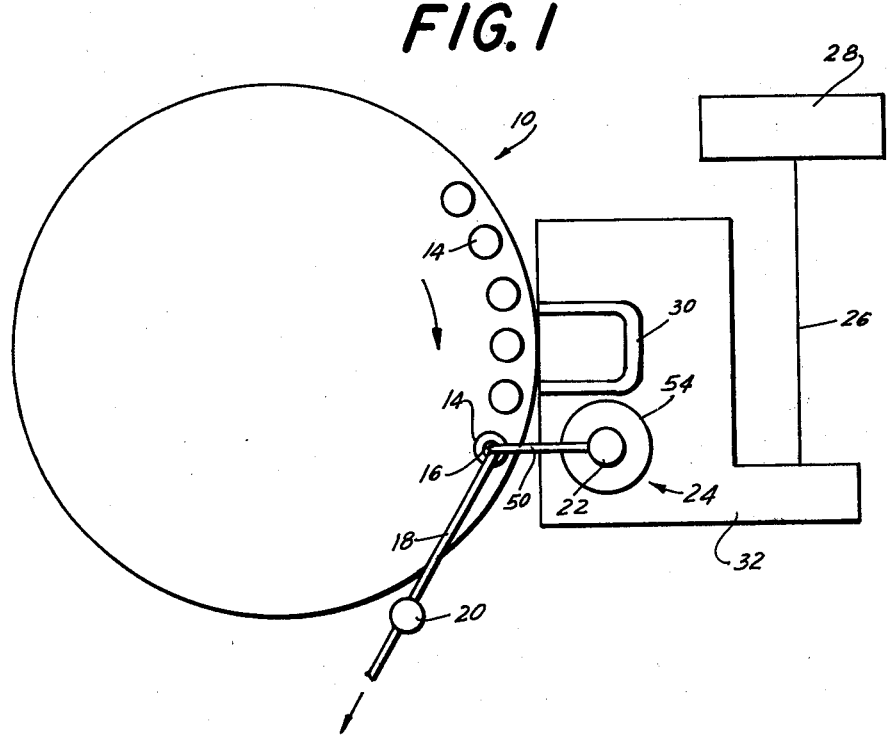
FIG. 1 is a plan view of a sampler having a probe drive mechanism embodying the invention.

In FIG. 1, a sampler is indicated generally at 10 which comprises a turntable 12 supporting in circular array a series of receptacles 14 which may support a series of different blood samples for analysis. The turntable 12 is driven in increments in a nonillustrated manner to successively present the receptacles 14 to an offtake station for access of an aspirating probe 16 to their liquid contents. The probe construction may consist only of a rigid tube to the outlet of which is coupled the inlet end of a flexible tube 18. A pump 20 is interposed in the tube 18 to pump fluid in the probe 16 to analysis, not shown, of a conventional automated type. The probe 16 is fixedly supported from one end portion of a vertical shaft 22 which is driven up and down for entry of the probe into the receptacles and also angularly, as will appear hereinafter.

In FIG. 1, the probe drive mechanism of the sampler is indicated generally at 24 and is coupled by a cable 26 to a programmer 28 by which the components of the drive mechanism 24 are operated, which components will be described. If desired, the self-washing probe assembly of FIG. 1 of Gordon and Adler U.S. Pat. No. 3,960,020, may be substituted for the probe 16. In that event, a liquid receptacle 39 fixed in stationary position on the sampler 10 may support a liquid standard for calibration of the non-illustrated analyzer. As the illustrated probe is not of the self-washing type, the receptacle 30 supports a wash solution for aspiration by the probe intermediate aspirations of liquids from successive receptacles 14, as will be described.

Turning now to the details of the probe driving mechanism of the form of FIG. 1, there is shown in the last-mentioned view an outer housing 32 within which there is a reversible electric motor 34 (FIG. 4) suitably supported from a plate 35 and controlled by the programmer 28. The motor 34, through a similarly controlled electro-magnetic clutch 36, may drive, through a driving member 37, either a screw element or a nut element threaded on the screw element, one of the elements carrying the probe shaft and being axially movable on the other, as previously indicated. In this illustrated form, the motor 34, through the clutch 36, drives the lead screw 38 which is axially fixed and preferably has a high lead angle such that one revolution of the screw 38 advances the nut 40 during up and down motions of the latter approximately 9/16 in. The screw 38 is a multi-thread element preferably having about 14 of such threads, or starts, and of conventional construction. The nut 40 is internally threaded to cooperate with the screw 38 and externally cooperates with a fixed, vertically arranged housing 42, within the housing 32, to prevent angular movement of the nut 40 for axial movement thereof along the screw 38. In the form illustrated by way of example, the nut 40 has on its pheriphery a fixed, vertically arranged key 44 extending radially outwardly from the element 40 to engage in one or the other of slots 46, 48 (FIG. 2) of the housing 42 for preventing rotation of the nut 40 during the vertical travel of the latter on the screw 38.

Figure 4:
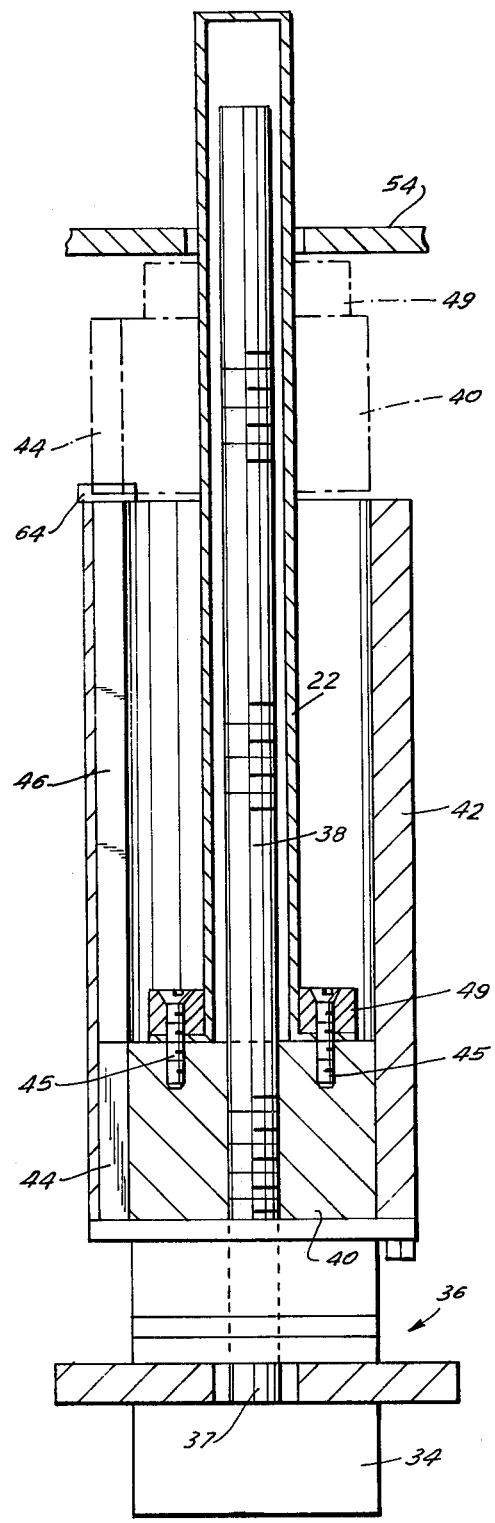
FIG. 4 is a sectional view on line 4—4 of FIG. 2.

In the condition of the parts shown in FIG. 4, the probe 16 is shown immersed in a sample receptacle 14 with the nut 40 in its lowermost position with the key 44 thereof located in the slot 46. In this view, the probe shaft 22 is shown as hollow, embracing with clearance the screw element 38 and flanged at the bottom for sandwiched attachment in fixed relation to the nut 40 as by bolts 45 extending through a collar 49, hereinafter referred to as the top of the nut 40. The shaft 22 has at its upper end portion a fixed horizontal arm 50 supporting the probe 16. When the probe 16 is immersed as shown, the probe 16 aspirates sample from the receptacle 14.

Figure 2:
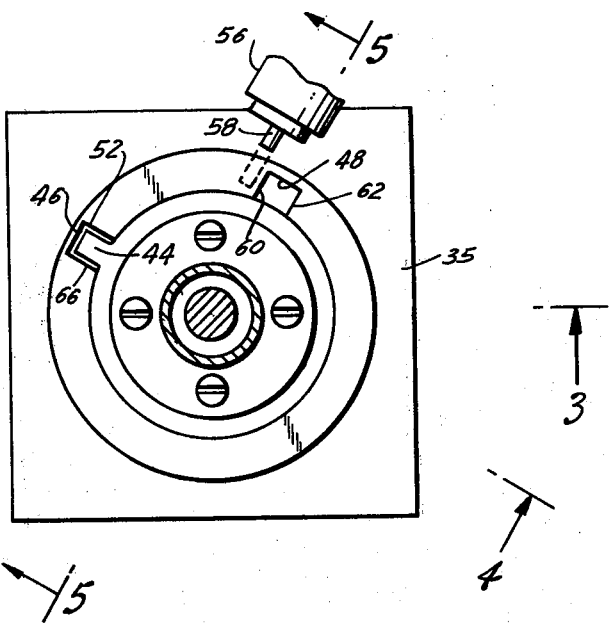
FIG. 2 is generally an enlarged plan view of a portion of the drive mechanism with certain parts being shown in section and other parts being omitted for a clearer understanding of the mechanism.
Figure 3:
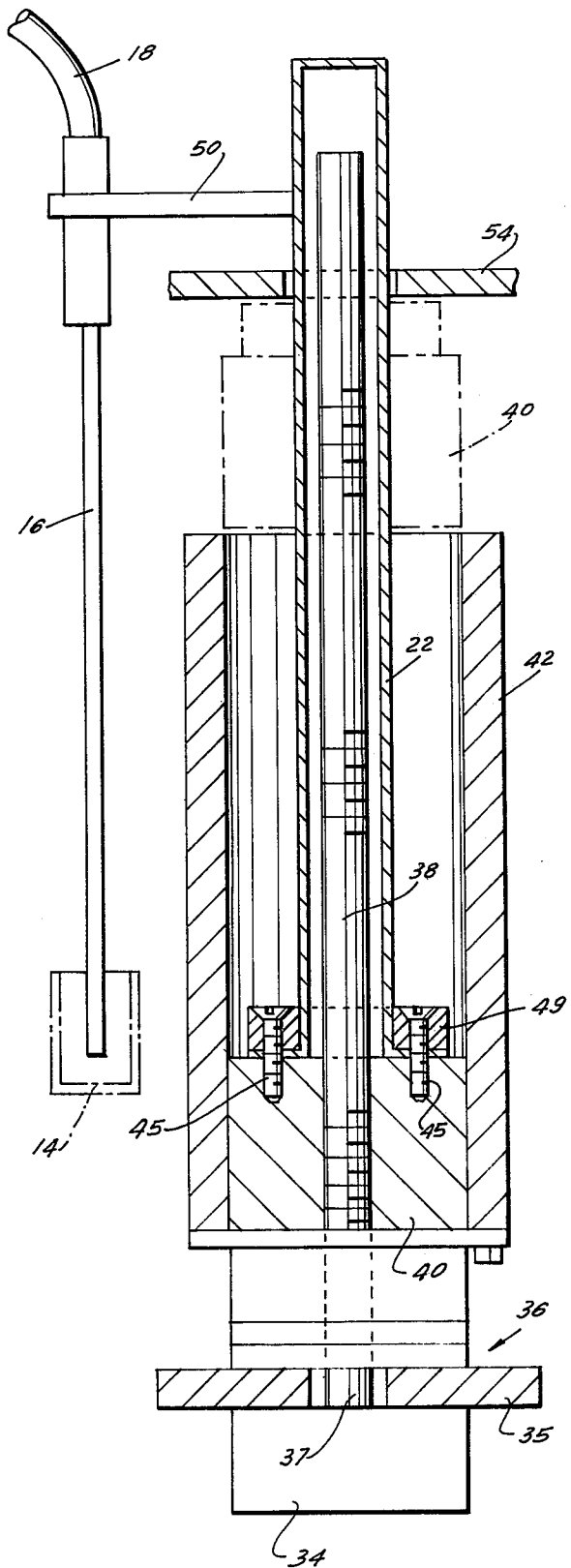
FIG. 3 is a sectional view on line 3—3 of FIG. 2.

When the motor 34 is energized and the clutch 36 engaged to drive the screw 38 in a clockwise direction as shown in FIG. 2, the nut 40 is driven upwardly in the housing 42 raising the probe 16 out of the receptacle 14 during which movement the probe 16 aspirates air. Further, during this movement, the key 44 may bear lightly and slidingly against the side 52 of the slot 46. A stationary stop plate 54, spaced a distance upwardly from the open upper end of the housing 42 and suitably supported, is provided to limit axial movement of the nut 40 and through which plate the probe shaft 22 moves with clearance in its movements with the nut 40. The underside of the plate 54 provides an abutment for the top of the nut 40 as the latter is driven upwardly and just clears the housing 42 with the key 44 leaving the slot 46. Upon this abutment with the plate 54 by the nut 40 and the clearance of the latter from the housing, while the screw 38 is rotating clockwise (FIG. 2), the nut 40 rotates bodily with the screw 38 significantly less than one revolution. Such rotation of the nut 40 with the screw 38 is terminated by release of the clutch 36 and deenergization of the motor 36, but is sufficient for the nut key 44 to rotate to an angular position slightly beyond the housing slot 48. Thereafter, a solenoid 56 is energized to extend a plunger 58 from the full line retracted position thereof shown in FIG. 2 to the extended broken line position. The clutch 36 is re-engaged and the motor 33 is energized once again but the motor is reversed to drive the screw 38 in a counterclockwise direction (FIG. 2). The nut 40 and screw 38 rotate bodily until the nut key 44 abuts the plunger 58 stopping angular movement of the nut 40. The plunger 58 is so located with reference to the housing slot 48 that when this contact takes place the key 44 is aligned with the slot 48 and the probe 16 is in registry with the wash receptacle 30 as shown in FIG. 5. Since further angular rotation of the nut 40 is inhibited, the last-mentioned rotation of the screw 28 is continued driving the nut 30 downwardly on the screw with the key 44 entering and sliding down the slot 48 which continues to restrain the nut against rotation. The solenoid 56 is deenergized, causing the plunger 58, which is spring biased, to retract. During this nut movement, the key 44 may slidingly engage the side 60 of the slot 48. When the probe 16 is immersed in the solution in the receptacle 30 and commences aspirating such solution, the clutch 36 is released and the motor 34 is de-energized, with the nut 40 in the lower position.

When sufficient solution has been aspirated in this manner, the clutch is re-engaged and the motor energized to drive the screw 38 in a clockwise direction (FIG. 2) driving the nut 40 and the probe 16 upwardly so that the latter once again aspirates air. During this upward movement, the key 44 may slidingly engage the side 62 of the slot 48. As before, on contact of the top of the nut 40 with the plate 54 and clearance of the key 44 with the slot 48, the nut 40 rotates bodily with the screw 38, a short angular distance significantly less than one revolution, until the screw 38 and the nut 40 are stopped by release of the clutch 36 and deenergizing of the motor 34 by the programmer 28. Immediately thereafter, the clutch 36 is re-engaged and the motor 34 is energized to drive the screw and nut bodily in the counterclockwise direction (FIG. 2), until the key 44 contacts and further rotation of the nut in this direction is restrained by a shoulder 64 on the housing providing an abutment for the key 44. The shoulder 64 (FIG. 4) is so located with reference to the slot 46 that when this contact by the key 44 occurs, the key is in alignment with the slot 46 and the probe 16 is in registry with the next successive receptacle 14 presented by the turntable 12 at the offtake station previously occupied by the receptacle 14 from which liquid was aspirated as described above. The turntable 12 is moved angularly one increment for such receptacle indexing with the offtake station subsequent to the probe 16 leaving one such receptacle 14. As before, the screw 38 continues to rotate in the counterclockwise direction (FIG. 2) while the nut 40, restrained from rotating with it, is driven downwardly with the key 44 entering and sliding along the slot 46. During this movement, the key may slidingly engage the side 66 (FIG. 2) of the slot 46 which side is flush with the shoulder 64. The pump 20 is operated continuously, and when the probe and nut are again in the lower position with the probe immersed in the liquid of the receptacle 14 in registry therewith the clutch 36 is released and the motor 34 deenergized while the liquid is aspirated by the probe. The above-described cycle of operation of the sampler wherein the liquids in the receptacles 14 may be different blood samples results in the flow of a stream in the tube 18 in which each sample is separated from its neighbor by two air segments having a wash solution segment therebetween.

It will be evident from the foregoing that when the probe 16 is in its lowermost position and aspirating sample, the probe-supporting nut 40 may be repeatedly raised and lowered a distance in the housing while the key remains in the slot 46 by repeated reversals of the direction of the motor 34 such that the probe 16 is alternately immersed and removed from the sample, if this is desired. Such sample "pecking", as this procedure is referred to, results in segments of sample alternating with segments of air in the probe 16, and occurs prior to the travel of the probe to the receptacle 30.

In the modified form of FIG. 6, the wash receptacle 30 of the sampler is omitted and the details of the probe 16, not shown, are preferably in accordance with aforementioned U.S. Pat. No. 3,960,020 so that the probe 16 is of the self-washing type. However, it is to be understood that probe details do not form a part of the present invention. The probe driving mechanism of FIG. 6 includes a housing 70 similar to the housing 42 previously described, but having a slot 72 therein which is generally vertical and having at the upper end thereof a lateral extension 75. As before, the screw 38, driven from the motor 34 through the clutch 36, extends upwardly in the housing 70 with clearance. Nut 74, similar to the previously described nut 40, is threaded on the screw 38 for cooperation with the housing 70. In this form, the nut 74 has on its periphery a fixed radially extending pin 76 extending into a housing slot 72 which slot limits the vertical movement of the nut in the housing and also the angular movement thereof as will be described. The probe shaft 22, the probe arm 50 and the probe 16 are fixed to the nut 74 in a manner similar to that previously decribed with reference to the form of FIG. 1. The pin 76, when in abutment with the lower extremity of the slot 72, determines the extreme lower position of the nut 74.

When the parts are in this condition, the probe 16 is immersed in the liquid of a receptacle 14 of the sampler as shown in FIG. 6. As before, the probe 16 aspirates the liquid contents of the receptacle 14 while the clutch 36 is released and the motor 34 is deenergized. When sufficient liquid is aspirated from the receptacle 14 by the probe 16, clutch 36 is engaged and the motor 34 energized to drive the screw in a clockwise direction. The pin 76 in the lower portion of the slot 72 prevents rotation of the nut 74 and the nut 74 is driven upwardly in the housing 70 causing the probe 16 to leave the receptacle 14 while travelling in an upward direction with the nut 74. When the pin 76 reaches the upper extremity of the vertical section of the slot 72, its vertical travel is terminated and the nut 74 is then free to rotate bodily with the shaft 38 to the extent of movement of the pin 76 permitted in the lateral extension 75 of the slot 72. The clutch 36 may be disengaged so that the nut 74 coasts to a stop position with the pin 76 contacting the right hand extremity (FIG. 6) of the extension 75. When the nut 74 is in the last-mentioned angular position, the probe 16 is in an angular position shown in broken lines in FIG. 6 wherein any drip from the lower end of the probe is not in registry with any of the receptacles 14 of the sampler, so there is no possibility of contamination of the liquids in any such receptacles 14, particularly the next successive receptacle 14 which is moved into the off-take position in the manner previously described. A suitable drip receptacle 78 may be in registry with the lower end of probe 16 when the probe 16 is in the broken-line rest position of FIG. 6. Subsequent to the probe 16 reaching this rest position, the clutch 36 is reengaged and the motor 34 energized to drive the screw 38 in the opposite direction, that is, in a counterclockwise direction as viewed in FIG. 6. Such rotation of the screw 36 effects movement therewith of the nut 74 until the pin 76 reaches the left extremity (FIG. 6) of the slot 72 at which time contact of the pin 76 with the slot 72 prevents further rotation of the nut with the screw and the nut is driven downwardly along the screw. During this movement, the pin 76 moves downwardly in the vertical portion of the slot 72. Just prior to the pin 76 reaching the lower extremity of the slot 72, the clutch 36 is released and the motor 34 is deenergized so that the pin 76 may coast to a position in abutment with the lower extremity of the slot 72. When the nut 74 is lowered in the housing in this manner, the probe 16 fixed thereto is immersed in the contents of the next receptacle 14. As before, the cycle may be repeated until the probe 16 has sampled the liquids of all the receptacles 14.

While plural forms of the probe drive mechanism have been illustrated and described, it will be apparent, especially to those versed in the art, that the invention is susceptible to other forms and changes in details without departing from the principles of the invention.

What is claimed is:

1. A sampler, comprising a liquid sampling probe, a first element, a second element having a vertical axis for movement therealong and threadedly cooperating with said first element, said second element supporting the probe for movement therewith, one of said elements comprising a nut, reversible means for rotating said first element in a first direction and a second direction to move said second element upwardly and downwardly, respectively, along said vertical axis and to rotate said second element to first and second angular positions, respectively, keying means for limiting the rotational movement of said second element during at least part of the upward and downward movement of said second element along said axis while in said first and second angular positions, first means and second means for limiting rotational movement of said second element to said first and second angular positions, respectively, and during rotation of said first element in said second direction, and means for positioning said second means upon rotation of said second element to said second angular position and operation of said reversible means to rotate said first element in said second direction.

2. Apparatus as defined in claim 1, wherein: said first element is said screw and is axially fixed, said second element being said nut.

3. Apparatus as defined in claim 1, further including a programmer controlling said reversals of said means rotating said first element.

4. Apparatus as defined in claim 3, wherein said programmer means includes means for operating said positioning means following rotation of said second element to said second angular position.

* * * * *